United States Patent
Mirigian et al.

(10) Patent No.: US 7,883,474 B1
(45) Date of Patent: *Feb. 8, 2011

(54) COMPOSITE BRAIDED GUIDEWIRE

(75) Inventors: Gregory E. Mirigian, Fremont, CA (US); Harold E. Carrison, Pleasanton, CA (US); Laurent Schaller, Los Altos, CA (US); Erik T. Engelson, Menlo Park, CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/640,259

(22) Filed: Apr. 30, 1996

Related U.S. Application Data

(63) Continuation-in-part of application No. 08/451,917, filed on May 26, 1995, now abandoned, which is a continuation-in-part of application No. 08/346,143, filed on Nov. 29, 1994, now abandoned, which is a continuation-in-part of application No. 08/062,456, filed on May 11, 1993, now Pat. No. 5,409,015.

(51) Int. Cl.
    *A61M 25/00* (2006.01)
(52) U.S. Cl. ...................................... 600/585
(58) Field of Classification Search ................. 600/585; 604/95, 90, 280, 281, 282
    See application file for complete search history.

(56) References Cited

U.S. PATENT DOCUMENTS

| | | | |
|---|---|---|---|
| 2,221,138 A | 6/1938 | Hendrickson |
| 2,279,297 A | 4/1942 | Bry |
| 2,905,178 A | 9/1959 | Hilzinger, III |
| 3,174,851 A | 3/1965 | Buehler et al. |
| 3,338,046 A | 8/1967 | Baur et al. |
| 3,351,463 A | 11/1967 | Rozner et al. |
| 3,416,531 A | 12/1968 | Edwards |
| 3,452,742 A | 7/1969 | Muller |

(Continued)

FOREIGN PATENT DOCUMENTS

EP 0014424 8/1980

(Continued)

OTHER PUBLICATIONS

Merriam-Webster's Collegiate Dictionary, 10th ed., Merriam-Webster, Incorporated, 2001, 335, 809.*

*Primary Examiner*—Max Hindenburg
*Assistant Examiner*—Jonathan M Foreman
(74) *Attorney, Agent, or Firm*—Seager, Tufte & Wickhem, LLC

(57) ABSTRACT

This is a composite guidewire for use with a catheter for accessing a targeted site in a lumen system of a patient's body. The guidewire core or guidewire section may be of a stainless steel or a high elasticity metal alloy, preferably a Ni—Ti alloy, also preferably having specified physical parameters. The composite guidewire assembly is especially useful for accessing peripheral or soft tissue targets. The invention includes multi-section guidewire assemblies having superelastic alloy or stainless steel ribbon braided reinforcements along a least a portion of the core. A variation of the inventive guidewire includes a braid and a tie layer (and one or more lubricious polymers on the tie layer exterior) to enhance the guidewire's suitability for use within catheters and within the interior of vascular lumen.

13 Claims, 4 Drawing Sheets

U.S. PATENT DOCUMENTS

| | | |
|---|---|---|
| 3,528,406 A | 9/1970 | Jeckel et al. |
| 3,547,103 A | 12/1970 | Cook |
| 3,552,384 A | 1/1971 | Pierie et al. |
| 3,753,700 A | 8/1973 | Harrison et al. |
| 3,757,768 A | 9/1973 | Kline |
| 3,789,841 A | 2/1974 | Antoshkiw |
| 3,941,119 A | 3/1976 | Corrales |
| 3,973,556 A | 8/1976 | Fleischhacker et al. |
| 4,003,369 A | 1/1977 | Heilman et al. |
| 4,020,829 A | 5/1977 | Willson et al. |
| 4,178,810 A | 12/1979 | Takahashi |
| 4,215,703 A | 8/1980 | Willson |
| 4,430,083 A | 2/1984 | Ganz et al. |
| 4,538,622 A | 9/1985 | Samson et al. |
| 4,545,390 A | 10/1985 | Leary |
| 4,554,929 A | 11/1985 | Samson et al. |
| 4,619,274 A | 10/1986 | Morrison |
| 4,665,906 A | 5/1987 | Jervis et al. |
| 4,721,117 A | 1/1988 | Mar et al. |
| 4,739,768 A | 4/1988 | Engelson |
| 4,770,188 A | 9/1988 | Chikama |
| 4,817,613 A * | 4/1989 | Jaraczewski et al. ......... 600/434 |
| 4,846,186 A | 7/1989 | Box et al. |
| 4,925,445 A | 5/1990 | Sakamoto et al. |
| 4,934,380 A | 6/1990 | de Toledo |
| 4,966,163 A | 10/1990 | Kraus et al. |
| 4,969,890 A | 11/1990 | Sugita et al. |
| 4,971,490 A | 11/1990 | Hawkins |
| 4,984,581 A | 1/1991 | Stice |
| 4,991,602 A | 2/1991 | Amplatz et al. |
| 4,998,923 A | 3/1991 | Samson et al. |
| 5,042,985 A | 8/1991 | Elliott et al. |
| 5,050,606 A | 9/1991 | Tremulis |
| 5,060,660 A * | 10/1991 | Gambale et al. ............ 600/585 |
| 5,069,226 A | 12/1991 | Yamauchi et al. |
| 5,095,915 A | 3/1992 | Engelson |
| RE33,911 E | 5/1992 | Samson et al. |
| 5,111,829 A | 5/1992 | Alvarez de Toledo |
| 5,120,308 A | 6/1992 | Hess |
| 5,129,890 A | 7/1992 | Bates et al. |
| 5,143,085 A | 9/1992 | Wilson et al. |
| 5,144,959 A | 9/1992 | Gambale et al. |
| 5,171,383 A | 12/1992 | Sagaye et al. |
| 5,213,111 A | 5/1993 | Cook et al. |
| 5,230,348 A | 7/1993 | Ishibe et al. |
| 5,238,004 A | 8/1993 | Sahatjian et al. |
| 5,251,640 A * | 10/1993 | Osborne ...................... 600/585 |
| 5,257,974 A * | 11/1993 | Cox ........................ 604/103.05 |
| 5,346,508 A * | 9/1994 | Hastings ...................... 607/99 |
| 5,365,943 A | 11/1994 | Jansen |
| 5,407,623 A | 4/1995 | Zachariades et al. |
| 5,409,015 A | 4/1995 | Palermo |
| 5,437,282 A | 8/1995 | Koger et al. |
| 5,452,726 A * | 9/1995 | Burmeister et al. ......... 600/585 |
| 5,498,250 A * | 3/1996 | Prather ...................... 604/529 |
| 5,505,725 A | 4/1996 | Samson |
| 5,534,007 A * | 7/1996 | St. Germain et al. ........ 606/108 |
| 5,540,707 A * | 7/1996 | Ressemann et al. ......... 606/159 |
| 5,549,109 A * | 8/1996 | Samson et al. .............. 600/381 |
| 5,596,996 A * | 1/1997 | Johanson et al. ............ 600/585 |
| 5,673,707 A * | 10/1997 | Chandrasekaran ......... 600/585 |
| 5,769,796 A * | 6/1998 | Palermo et al. ............. 600/585 |

FOREIGN PATENT DOCUMENTS

| | | | |
|---|---|---|---|
| EP | 0 382 974 A1 * | 4/1989 | |
| EP | 0382974 | 8/1990 | |
| EP | 0491349 | 6/1992 | |
| EP | 0515201 | 11/1992 | |
| EP | 0519604 | 12/1992 | |
| EP | 0 661 073 | 7/1995 | |
| JP | 02029266 A * | 1/1990 | |
| JP | 0407965 * | 1/1991 | |
| WO | WO 91/15152 | 10/1991 | |

* cited by examiner

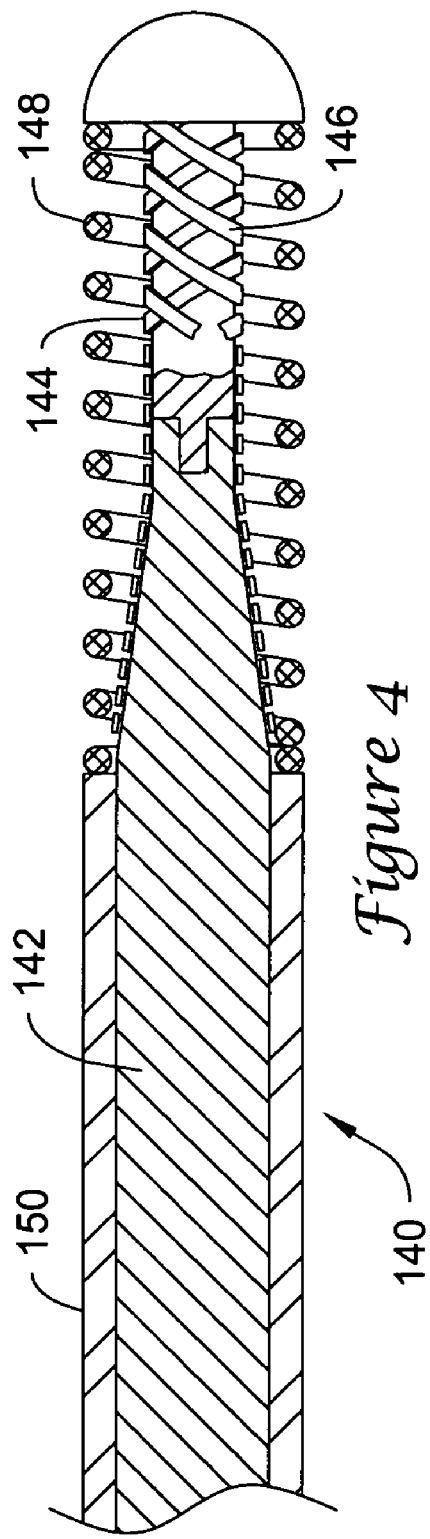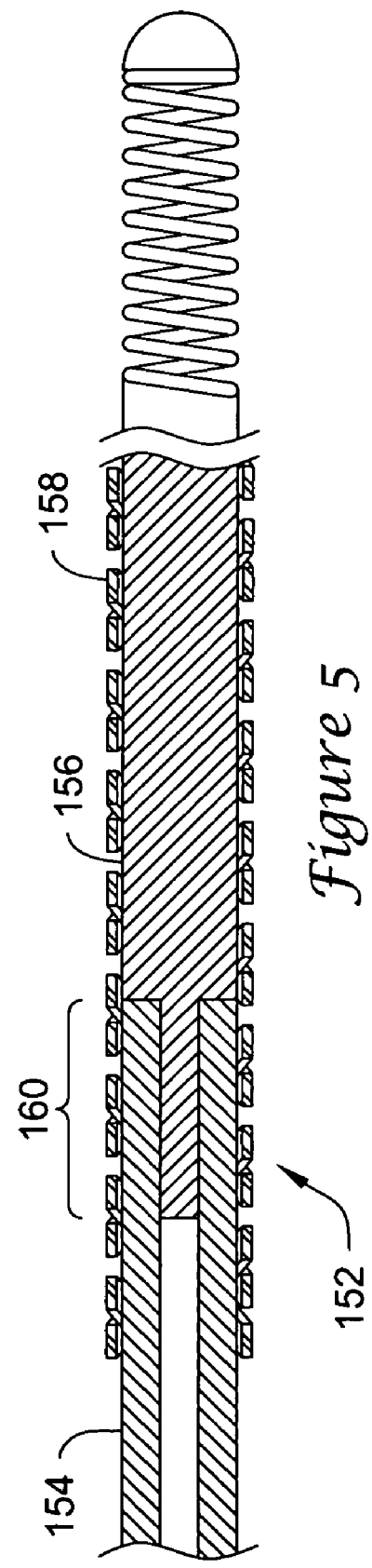

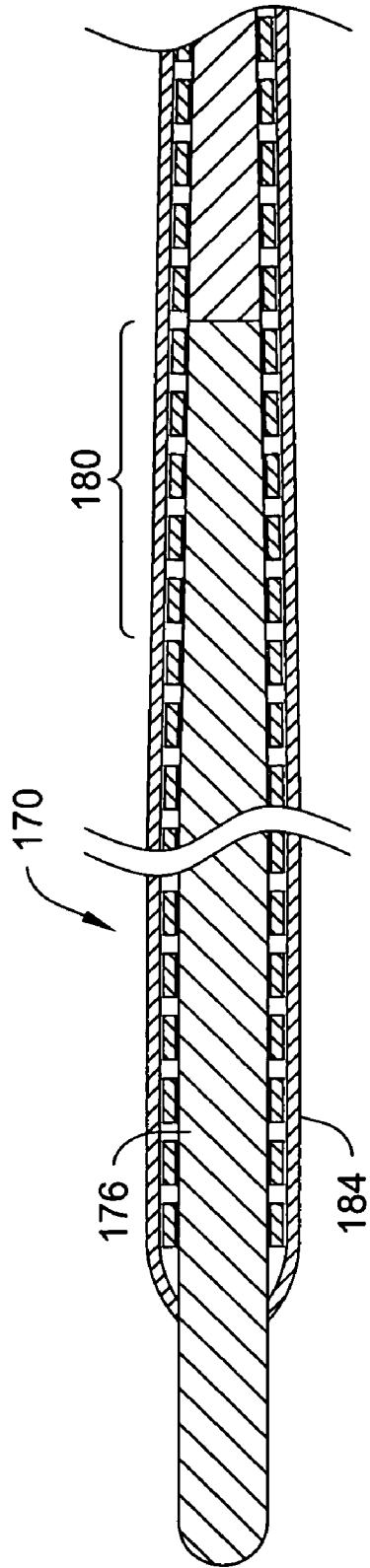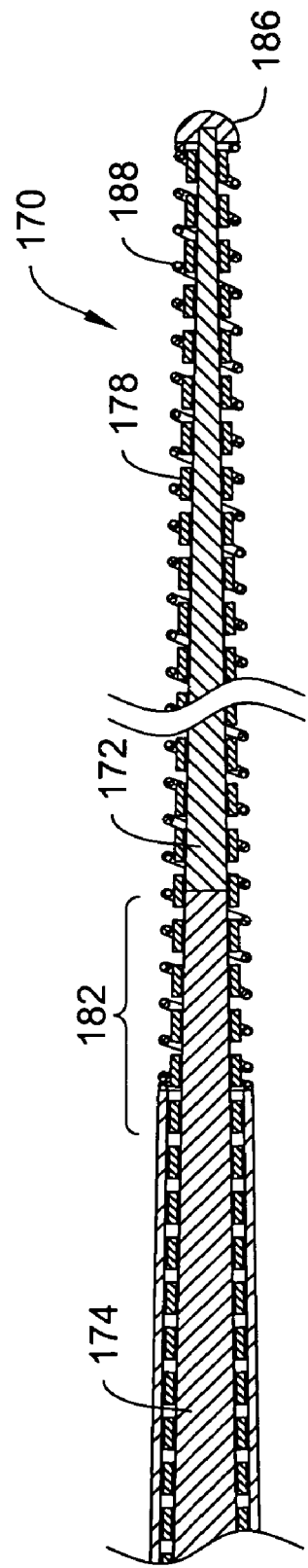

COMPOSITE BRAIDED GUIDEWIRE

RELATED APPLICATIONS

This is a continuation-in-part of U.S. Ser. No. 08/451,917, filed May 26, 1995, abandoned, which in turn is a continuation-in-part of U.S. Ser. No. 08/346,143, filed Nov. 29, 1994, abandoned, which in turn is a continuation-in-part of U.S. Ser. No. 08/062,456, filed May 11, 1993, now U.S. Pat. No. 5,409,015, issued Apr. 25, 1995.

FIELD OF THE INVENTION

This invention is a surgical device. It is a composite guidewire for use in a catheter and is used for accessing a targeted site in a lumen system of a patient's body. The guidewire core or guidewire section may be of a stainless steel or a high elasticity metal alloy, preferably a Ni—Ti alloy, also preferably having specified physical parameters. The composite guidewire assembly is especially useful for accessing peripheral or soft tissue targets. The invention includes multi-section guidewire assemblies having super-elastic alloy or stainless steel ribbon braided reinforcements along a least a portion of the core. A variation of the inventive guidewire includes a braid of the exterior of the core wire with a tie layer and one or more lubricious polymers on the exterior to enhance the guidewire's suitability for use within catheters and within the interior of vascular lumen.

BACKGROUND OF THE INVENTION

Catheters are used increasingly as a means for delivering diagnostic and therapeutic agents to internal sites within the human body that can be accessed through the various of the body's lumen systems, particularly through the vasculature. A catheter guidewire is used for guiding the catheter through the bends, loops, and branches forming the blood vessels within the body. One method of using a guidewire to direct the catheter through the torturous paths of these systems of lumen involves the use of a torqueable guidewire which is directed as a unit from a body access point such as the femoral artery to the tissue region containing the target site. The guidewire is typically bent at its distal end, and may be guided by alternately rotating and advancing the guidewire along the small vessel pathway to the desired target. Typically the guidewire and the catheter are advanced by alternately moving the guidewire along a distance in the vessel pathway, holding the guidewire in place, and then advancing the catheter along the axis of the guidewire until it reaches the portion of the guidewire already advanced farther into the human body.

The difficulty in accessing remote body regions, the body's periphery or the soft tissues within the body such as the brain and the liver, are apparent. The catheter and its attendant guidewire must be both flexible, to allow the combination to follow the complicated path through the tissue, and yet stiff enough to allow the distal end of the catheter to be manipulated by the physician from the external access site. It is common that the catheter is as long as a meter or more.

The catheter guidewires used in guiding a catheter through the human vasculature have a number of variable flexibility constructions. For instance, U.S. Pat. Nos. 3,789,841; 4,545, 390; and 4,619,274 show guidewires in which the distal end section of the wire is tapered along its length to allow great flexibility in that remote region of the guidewire. This is so, since the distal region is where the sharpest turns are encountered. The tapered section of the wire is often enclosed in a wire coil, typically a platinum coil, to increase the column strength of the tapered wire section without significant loss of flexibility in that region and also to increase the radial capacity of the guidewire to allow fine manipulation of the guidewire through the vasculature.

Another effective guidewire design is found in U.S. Pat. No. 5,095,915 which shows a guidewire having at least two sections. The distal portion is encased in an elongated polymer sleeve having axially spaced grooves to allow increased bending flexibility of the sleeve.

Others have suggested the use of guidewires made of various super-elastic alloys in an attempt to achieve some of the noted functional desires.

U.S. Pat. No. 4,925,445, to Sakamoto et al., suggests the use of a two-portion guidewire having a body portion relatively high in rigidity and a distal end portion which is comparatively flexible. At least one portion of the body and the distal end portions is formed of super-elastic metallic materials. Although a number of materials are suggested, including Ni—Ti alloys of 49 to 58% (atm) nickel, the patent expresses a strong preference for Ni—Ti alloys in which the transformation between austentite and martensite is complete at a temperature of 10° C. or below. The reason given is that "for the guidewire to be useable in the human body, it must be in the range of 10° to 20° C. due to anesthesia at a low body temperature." The temperature of the human body is typically about 37° C.

Another document disclosing a guidewire using a metal alloy having the same composition as a Ni—Ti super-elastic alloy is WO91/15152 (to Sahatjian et al. and owned by Boston Scientific Corp.). That disclosure suggests a guidewire made of the precursor to the Ni—Ti elastic alloy. Super-elastic alloys of this type are typically made by drawing an ingot of the precursor alloy while simultaneously heating it. In the unstressed state at room temperature, such super-elastic materials occur in the austenite crystalline phase and, upon application of stress, exhibit stress-induced austenite-martensite (SIM) crystalline transformations which produce nonlinear elastic behavior. The guidewires described in that published application, on the other hand, are said not to undergo heating during the drawing process. The wires are cold-drawn and great pain is taken to assure that the alloy is maintained well below 300° F. during each of the stages of its manufacture. This temperature control is maintained during the step of grinding the guidewire to form various of its tapered sections.

U.S. Pat. No. 4,665,906 suggests the use of stress-induced martensite (SIM) alloys as constituents in a variety of different medical devices. Such devices are said to include catheters and cannulas.

U.S. Pat. No. 4,969,890 to Sugita et al., suggests the production of a catheter having a main body fitted with a shape memory alloy member, and having a liquid injection means to supply a warming liquid to allow the shape memory alloy member to recover its original shape upon being warmed by the fluid.

U.S. Pat. No. 4,984,581, to Stice, suggests a guidewire having a core of a shape memory alloy, the guidewire using the two-way memory properties of the alloy to provide both tip-deflecting and rotational movement to the guidewire in response to a controlled thermal stimulus. The controlled thermal stimulus in this instance is provided through application of an RF alternating current. The alloy selected is one that has a transition temperature between 36° C. and 45° C. The temperature 36° C. is chosen because of the temperature of the human body; 45° C. is chosen because operating at higher temperatures could be destructive to body tissue, particularly some body proteins.

U.S. Pat. No. 4,991,602 to Amplatz et al., suggests a flexible guidewire made up of a shape memory alloy such as the nickel-titanium alloy known as nitinol. The guidewire is one having a single diameter throughout its midcourse, is tapered toward each end, and has a bead or ball at each of those ends. The bead or ball is selected to allow ease of movement through the catheter into the vasculature. The guidewire is symmetrical so that a physician cannot make a wrong choice in determining which end of the guidewire to insert into the catheter. The patent suggests that wound wire coils at the guidewire tip are undesirable. The patent further suggests the use of a polymeric coating (PTFE) and an anticoagulant. The patent does not suggest that any particular type of shape memory alloy or particular chemical or physical variations of these alloys are in any manner advantageous.

Another catheter guidewire using Ni—Ti alloys is described in U.S. Pat. No. 5,069,226, to Yamauchi, et al. Yamauchi et al. describes a catheter guidewire using a Ni—Ti alloy which additionally contains some iron, but is typically heat-treated at a temperature of about 4000 to 5000 C so as to provide an end section which exhibits pseudo-elasticity at a temperature of about 370 C and plasticity at a temperature below about 800 C. A variation is that only the end portion is plastic at the temperatures below 800 C.

U.S. Pat. No. 5,171,383, to Sagae, et al., shows a guidewire produced from a super-elastic alloy which is then subjected to a heat treatment such that the flexibility is sequentially increased from its proximal portion to its distal end portions. A thermoplastic coating or coil spring may be placed on the distal portion of the wire material. Generally speaking, the proximal end portion of the guidewire maintains a comparatively high rigidity and the most distal end portion is very flexible. The proximal end section is said in the claims to have a yield stress of approximately five to seven kg/mm$^2$ and an intermediate portion of the guidewire is shown in the claims to have a yield stress of approximately 11 to 12 kg/mm$^2$.

Published European Patent Application 0,515,201-A1 also discloses a guidewire produced at least in part of a super-elastic alloy. The publication describes a guidewire in which the most distal portion can be bent or curved into a desired shape by a physician immediately prior to use in a surgical procedure. Proximal of the guide tip, the guidewire is of a super-elastic alloy. Although nickel-titanium alloys are said to be most desirable of the class shown in that disclosure, no particular physical description of those alloys is disclosed to be any more desirable than another.

Published European Patent Application 0,519,604-A2 similarly discloses a guidewire which may be produced from a super-elastic material such as nitinol. The guidewire core is coated with a plastic jacket, a portion of which may be hydrophilic and a portion of which is not.

Examples of Ni—Ti alloys are disclosed in U.S. Pat. Nos. 3,174,851; 3,351,463; and 3,753,700.

None of these disclosures suggest the guidewire configuration described below.

SUMMARY OF THE INVENTION

This invention is a guidewire, preferably a guidewire suitable for introduction into the vasculature of the brain, and a method for its use. The guidewire is of two particular components and may comprise others. The first component is a core wire of either a superelastic alloy or a stainless steel. The second component is a ribbon braid also of either a superelastic alloy or a stainless steel.

Desirable super-elastic alloys includes Ni—Ti alloys and particularly those having specific physical characteristics, e.g., a stress-strain plateau at about 75±10 ksi and another at 25±7.5 ksi (each measured at 3% strain) when the stress-strain relationship is measured to a strain of 6%.

A highly desirable variation of the inventive guidewire comprises a long wire having a proximal section, an intermediate section, and a distal section. The guidewire further may have an eccentricity ratio of 1±10$^{-4}$. The distal end section is typically the most flexible of the sections and is often at least about three centimeters long. The flexible distal end section may be partially tapered and covered by a coil assembly which is connected to the distal end of the guidewire at its distal tip. The coil assembly may be attached to the distal tip by soldering, perhaps after plating or coating the distal end section with a malleable or solderable metal, such as gold.

The guidewire with its braid covering may be coated or covered with a polymer or other material to enhance its ability to traverse the lumen of the catheter. A lubricious polymer may be placed directly upon the core wire or upon a "tie" layer. The tie layer may be a shrink-wrap tubing or a plasma deposition or may be a dip, spray, or fusion spray coating of an appropriate material. The tie layer may also be radio opaque.

One desirable composite involves a distal core portion of a super-elastic alloy and a more proximal section or sections of another material or configuration, e.g., stainless steel wire or rod, stainless steel hypotube, super-elastic alloy tubing, carbon fiber tubing, etc.

Ideally, there will be one or more radiopaque markers placed upon the guidewire, e.g., at its distal tip and potentially along the length of the intermediate section. These markers may be used both to enhance the guidewire's radiopacity and its ability to transmit torque from the proximal end to the distal end while maintaining a desired flexibility.

This invention also includes a catheter apparatus made up of the guidewire core and a thin-walled catheter designed to be advanced along the guidewire through the vasculature for positioning at a desired site.

BRIEF DESCRIPTION OF THE DRAWINGS

FIGS. 4 and 5 are partial cutaway side views of portions of various guidewires made according to the invention having composite cores.

FIGS. 6A and 6B together form a partial cutaway side-view of a composite guidewire made according to the invention.

DESCRIPTION OF THE INVENTION

Figure 1:
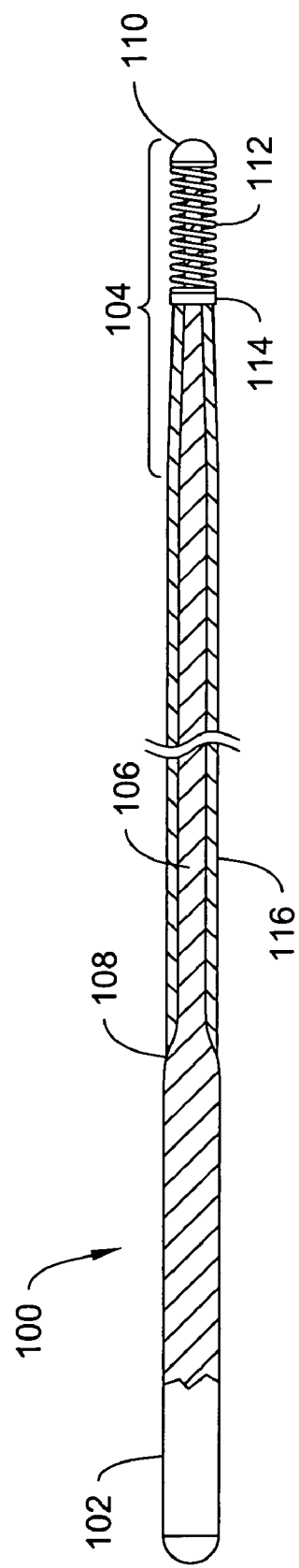
FIG. 1 shows a schematic side view (not to scale) of the major components of the inventive guidewire.

FIG. 1 shows an enlarged side view of a guidewire made according to the invention. The guidewire (100) is made up of the wire core formed of a flexible torqueable wire filament material and has a total length typically between about 50 and 300 centimeters. The proximal section (102) preferably has a uniform diameter (along its length) of about 0.010 to 0.025 inches, preferably 0.010 to 0.018 inches. The relatively more flexible distal section (104) extends for 3 to 30 centimeters or more of the distal end of the guidewire (100). There may be a middle section (106) having a diameter intermediate between the diameter of the two portions of the wire adjoining the middle section. The middle section (106) may be continuously tapered, may have a number of tapered sections or sections of differing diameters, or may be of a uniform diameter along its length. If middle section (106) is of a generally uniform diameter, the guidewire core will neck down as is seen at (108). The distal section (104) of the guidewire (100) typically has an end cap (110), a fine wire coil (112), and a solder joint (114). The fine wire coil (112) may be radiopaque and made from materials including but not limited to platinum and its alloys. The end cap (110) may be radiopaque to allow knowledge of the position of the coil (112) during the process of inserting the catheter and traversal of the guidewire through the vasculature.

At least some portion of the guidewire core has included thereon a braid placed generally on the outside surface of the core and often extends to the distal tip of the core. This braid is not seen in FIG. 1 but will be discussed in more detail below. The braid is constructed of a number of ribbons and, in general, is typically metallic. Preferred as ribbon materials are stainless steels and superelastic alloys, but high performance polymers such as polyaramids are useful in some situations.

All or part of the guidewire proximal section (102) and middle section (106) and distal section (104) may be coated with a thin layer (116) of polymeric material to improve its lubricity without adversely affecting the flexibility or shape-ability of the guidewire. This invention includes portions or sections of the guidewire described above having the noted polymeric tie layer described below and a slippery, e.g., a hydrophilic polymeric coating thereon.

Figures 2, 3:
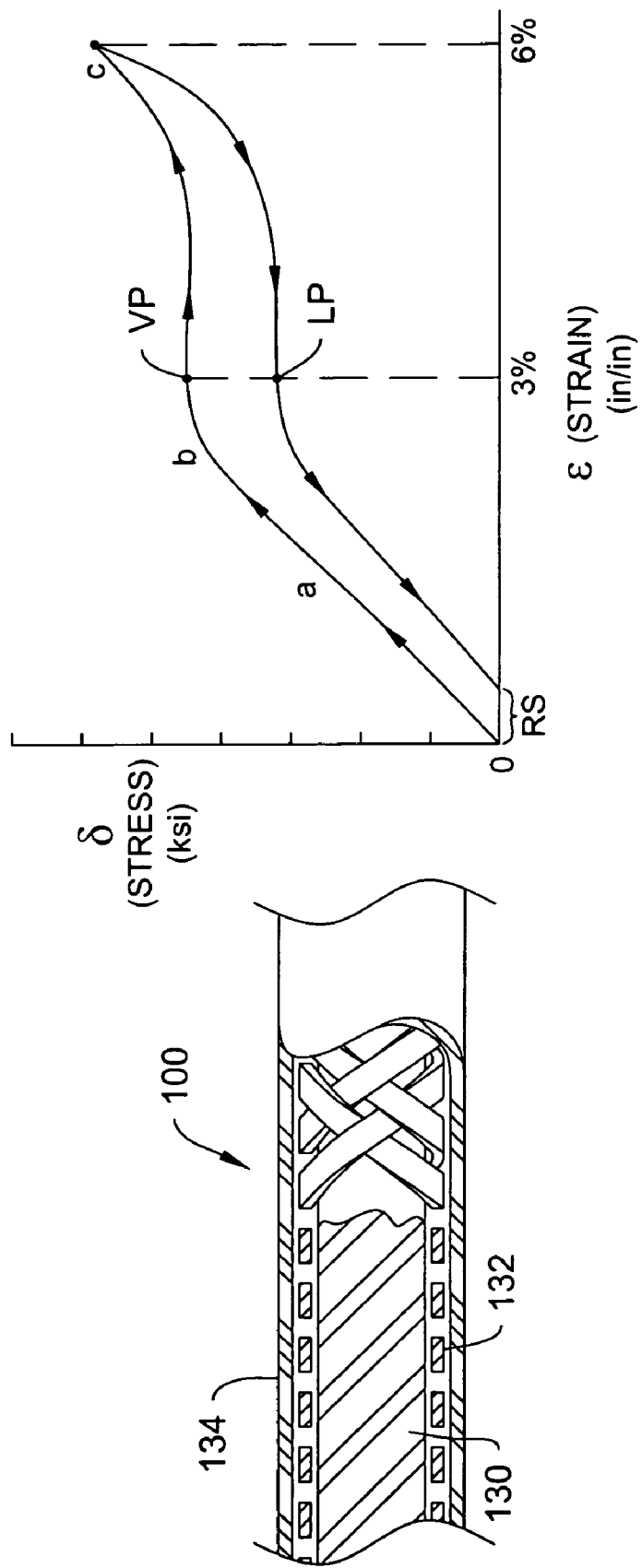
FIG. 2 is a partial cutaway side view of a guidewire having a braid covering distally.
FIG. 3 shows a typical stress-strain diagram for a Ni—Ti alloy displaying objective criteria for selection of alloys for the inventive guidewire.

FIG. 2 shows a partial cutaway of the inventive guidewire (100) showing the core wire (130), the supporting ribbon braid (132), and the polymeric covering (134). Not shown in FIG. 2 because it is only a very thin layer, is the applied polymeric (often hydrophilic polymeric) coating exterior to the polymeric covering (134). As is noted elsewhere, this structure may be placed in any portion of the final guidewire assembly.

Guidewire Core

The inventive guidewire assembly is typically used in a catheter which is made up of an elongate tubular member having proximal and distal ends. The catheter is about 50 to 300 centimeters in length, typically between about 100 and 200 centimeters in length. Often, the catheter tubular member has a relatively stiff proximal section which extends along a major portion of the catheter length and one or more relatively flexible distal sections which provide greater ability of the catheter to track the guidewire through sharp bends and turns encountered as the catheter is advanced through the torturous paths found in the vasculature. The construction of a suitable catheter assembly having differential flexibility along its length is described in U.S. Pat. No. 4,739,768.

Super-elastic alloys, particularly Ni—Ti alloys, retain their super-elastic properties during traversal through the vasculature and yet are sufficiently pliable that they provide the physician using the guidewire with enhanced "feel" or feedback and yet do not "whip" during use. That is to say, as a guidewire is turned it stores energy during as a twist and releases it precipitously as it "whips" to quickly recover the stored stress. The preferred alloys do not incur significant unrecovered strain during use. We have also found that if the eccentricity of the wire, i.e., the deviation of the cross-section of the guidewire from "roundness" (particularly in the middle section) is maintained at a very low value, the guidewire is much easier to steer or direct through the vasculature.

The material used in the guidewires of this invention are of shape memory alloys which exhibit super-elastic/pseudo-elastic shape recovery characteristics. These alloys are known. See, for instance, U.S. Pat. Nos. 3,174,851 and 3,351,463 as well as 3,753,700; the '700 patent describes a material because of the higher modulus of the material due to an increased iron content. These metals are characterized by their ability to be transformed from an austenitic crystal structure to a stress-induced martensitic (SIM) structure at certain temperatures, and return elastically to the austenitic structure when the stress is removed. These alternating crystalline structures provide the alloy with its super-elastic properties. One such well-known alloy, nitinol, is a nickel-titanium alloy. It is readily commercially available and undergoes the austenite-SIM-austenite transformation at a variety of temperature ranges between −20° C. and 30° C.

These alloys are especially suitable because of their capacity to elastically recover almost completely to the initial configuration once the stress is removed. Typically there is little plastic deformation, even at relatively high strains. This allows the guidewire to undertake substantial bends as it passes through the body's vasculature, and yet return to its original shape once the bend has been traversed without retaining any hint of a kink or a bend. Nevertheless, compared to similar stainless steel guidewires, less force need be exerted against the interior walls of the vessels to deform the guidewire of the invention along the desired path through the blood vessel thereby decreasing trauma to the interior of the blood vessel and reducing friction against the coaxial catheter.

A guidewire, during its passage through the vasculature to its target site, may undertake numerous bends and loops. The desirably of enhancing the ease with which a guidewire may be twisted to allow the bent distal tip to enter a desired branch of the vasculature cannot be overstated. We have found that one factor in enhancing such ease of use, that is, in enhancing the controllability of the guidewires is by controlling the eccentricity of the cross-section of the middle portion of the guidewire. We have found that by maintaining the middle portion of the guidewire (106 in FIG. 1) to an eccentricity ratio of $1 \pm 10^{-4}$, the guidewire is significantly more controllable than those which fall outside this ratio. By "eccentricity", we mean that at any point along the guidewire the ratio of the largest diameter at that cross-section to the smallest diameter of the wire at that cross-section.

To achieve these results of high strength and enhanced control even while allowing feedback to the attending physician during use, we have found that the following physical parameters of the alloy are suitable. In a stress-strain test as shown on a stress-strain diagram such as that found in FIG. 3 the stress found at the midpoint of the upper plateau (UP) (measured, e.g. at about 3% strain when the test end point is about 6% strain) should be in the range of 75 ksi (thousand pounds per square inch)±10 ksi and, preferably, in the range of 75 ksi±5 ksi. Additionally, this material should exhibit a lower plateau (LP) of 25±7.5 ksi, preferably 20±2.5 ksi, measured at the midpoint of the lower plateau. The material preferably has no more than about 0.25% residual strain (RS) (when stressed to 6% strain and allowed to return) and preferably no more than about 0.15% residual strain.

The preferred material is nominally 50.6%±0.2% Ni and the remainder Ti. The alloy should contain no more than about 500 parts per million of any of O, C, or N. These alloys often contain up to about 7% of one or more members of the iron group of metals, e.g., Fe, Cr, Co, etc. Typically such commercially available materials will be sequentially mixed, cast, formed, and separately co-worked to 30-40%, annealed and stretched.

By way of further explanation, FIG. 3 shows a stylized stress-strain diagram showing the various parameters noted above and their measurement on that diagram. As stress is initially applied to a sample of the material, the strain is at first proportional (a) until the phase change from austentite to martensite begins at (b). At the upper plateau (UP), the energy introduced with the applied stress is stored during the formation of the quasi-stable martensite phase or stress-induced-martensite (SIM). Upon substantial completion of the phase change, the stress-strain relationship again approaches a proportional relationship at (c). The stress is no longer applied when the strain reaches 6%. The measured value (UP) is found at the midpoint between zero and 6% strain, i.e., at 3% strain. If another terminal condition of strain is chosen, e.g., 7%, the measured valued of (UP) and (LP) would be found at 3.5%.

Materials having high UP values produce guidewires which are quite strong and allow exceptional torque transmission but cause a compromise in the resulting "straightness" of the guidewire. We have found that guidewires having high UP values in conjunction with high LP values are not straight. These guidewires are difficult to use because of their tendency to "whip" as they are turned. Again, that is to say, as a guidewire is turned it stores energy during as a twist and releases it quickly. The difficulty of using such a whipping guidewire should be apparent. Materials having UP values as noted above are suitable as guidewires.

Furthermore, materials having values of LP which are high, again, are not straight. Lowering the value of LP compromises the ability of the guidewire to transmit torque but improves the ease with which a straight guidewire may be produced. Lowering the LP value too far, however, results in a guidewire which, although round, has poor tactile response. It feels somewhat "vague" and "soupy" during its use. The LP values provided for above allow excellent torque transmission, straightness, and the valuable tactile response.

The values of residual strain discussed above define materials which do not kink or otherwise retain a "set" or configuration after stress during use as a guidewire.

In addition to the core wires made of super-elastic alloys, this invention also covers guidewire cores comprising various stainless steels. suitable stainless steels include those typically used in medical devices, e.g., 304SS, 306SS, 312SS, and 316SS. Most preferred are 304SS and 316SS. In comparison to the guidewire cores made of superelastic alloys, comparable stainless steel cores are more able to transmit torque and are typically stiffer. The trade-off is that stainless steels are much more likely to lack the elasticity of the super-elastic alloys.

The core may be an assembly of components such as is shown in FIGS. 4 and 5. These Figures depict only a few of the various arrangements contemplated under this invention. FIG. 4 shows a guidewire assembly having a composite core made up of a superelastic alloy portion (142) and a stainless steel distal section (144). The braid (146) in this instance might be a superelastic alloy. A radio-opaque coil (148) is also seen in the drawing. A polymeric covering (150) is also visible in the drawing. This combination of metallic components has the following benefits: the small stainless steel distal section (144) is readily shapeable by a physician using the device; the superelastic braid (146) inhibits the guidewire section containing the small stainless steel distal section (144) from kinking; the more proximal superelastic section does not kink during the manipulation necessary to introduce the guidewire to the target site.

Another desirable variation of a composite core wire (152) is seen in FIG. 5. In this variation, the more proximal section (154) is stainless steel to provide proximal stiffness. A tubing member is depicted but a solid core member may be used with some provision for a joint to the adjoining superelastic alloy section (156). An exterior braiding (158) is also shown. That braiding may be a stainless steel for stiffness, a superelastic alloy for kink resistance (particularly within the joint region (160)), or even a radio-opaque metal or alloy to allow observance of the guidewire during passage within the body.

This invention involves, in large part, the melding of the optimum qualities of the various physical parameters of the respective alloys to result in a guidewire assembly with greater overall effectiveness.

FIGS. 6A and 6B together depict a preferred embodiment of the invention. It is a guidewire including a composite core having sections of various alloys and specifically has a stainless steel distal tip section (172) to allow that tip to be easily shaped by the user. The middle portion (174) of the guidewire comprises a super-elastic alloy. The mid-section (174) passes through a significant length of the most tortuous vasculature during a procedure and hence is the most significant candidate for that alloy. The most proximal section (176) is used primarily for pushing and for transmitting twisting ("torquing") motions between the proximal end and the distal end. Consequently, the choice for materials in the more-proximal end (176) is often stainless steel. If a more flexible path is to be accessed in the vasculature, the choice of materials for the more-proximal end (176) may be a super-elastic alloy. Also depicted in the preferred embodiment in FIGS. 6A and 6B is a ribbon braid member (178) placed concentrically about the core wire. The braid (178) need not be the complete length of the core; it need be only over the portion requiring the enhanced physical characteristic. For instance, in procedures through vasculature having great tortuosity near a major vessel, e.g., liver vasculature, the proximal section need not be reinforced with a braid. The braid may variouly be a super-elastic alloy such as nitinol, a stainless steel, a polymeric material such as is noted elsewhere here, carbon fiber, etc. Preferred are superelastic alloys and stainless depending upon the usage.

The core assembly depicted in FIGS. 6A and 6B is typical of guidewires used to access targets in the vasculature of the brain. It however is only "typical" and forms no critical portion of the invention. The core assembly has two tapering regions (180, 182) to help with the transition between various regions of the core. As can be seen in the Figures, the tubular braid follows the core wire such that the maximum radial gap between the tubular braid and the core wire is less than the wall thickness of the tubular braid. The core wire may taper for significant regions or over short distances. Such decisions are within the purview of the guidewire designer. Similarly, selection of a polymeric coating (184) is a matter of choice for the designer. The distal tip (186) and radio-opaque coil (188) are relatively common features on contemporary guidewires.

Braids

The braids used in this invention are exterior to the surface of the guidewire core and are used to provide specific physical strengths of various types, e.g., torsional rigidity, stiffness, kink resistance, composite elasticity, etc. The braid may be placed directly upon the wire core or may be used with a thin layer of a polymer between the braid and core wire to provide a level of adhesion between the two. Other methods of bonding the braid to the core may be used, e.g., gluing, soldering, welding, etc. and the bonding may be continuous or at intervals along the core body.

Although the braid (132) most desired is shown in FIG. 2 and, has a single size of ribbon, the braid need not be so limited; multiple sizes of ribbon may be used as desired. The major limitations are simply the size, e.g., diameter, of the overall braid as finally constructed and the desired added stiffness to be added to the guidewire.

The braids typically useful in this invention comprise an even number of ribbons: one half of the ribbons wound one way, i.e., clockwise, and the remainder are wound the other way. A typical braid will be of eight to 16 ribbons. The braid may have a single pitch, an angle of a constituent ribbon measured against the axis of the braid, or it may have a pitch which varies along the axis of the braid.

Preferred super-elastic alloys include the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. Commercial alloys containing up to about 5% of one or more other members of the iron group, e.g., Fe, Cr, Co, are considered to be encompassed within the class of superelastic Ni/Ti alloys suitable for this service.

When using a superelastic alloy, an additional step may be desirable to preserve the shape of the stiffening braid. For instance, with a Cr-containing Ni/Ti superelastic alloy which has been rolled into a 1×4 mil ribbon and formed into a 16-member braid, some heat treatment is desirable. The braid is placed onto a mandrel, usually metallic, of an appropriate size. The braid is then heated to a temperature of 650°-750° F. for a few minutes, possibly (but not necessarily) annealing the constituent ribbon. After heat treatment, the braid retains its shape and the alloy retains its superelastic properties. The braid may also be wound directly onto the core if so desired.

Metallic ribbons that are suitable for use in this invention are desirably between 0.25 mil and 3.5 mil in thickness and 2.5 mil and 12.0 mil in width. By the term "ribbon", we intend to include elongated shapes, the cross-section of which are not square or round and may typically be rectangular, oval or semi-oval. They should have an aspect ratio of at least 0.5 (thickness/width). In any event, for superelastic alloys, particularly nitinol, the thickness and width may be somewhat finer, e.g., down to 0.25 mil and 1.0 mil, respectively. Currently available ribbons include sizes of 1 mil×3 mil, 1 mil×4 mil, 2 mil×6 mil, and 2 mil×8 mil.

The ribbons making up the braid (206) shown in FIG. 2 may also contain a minor amount of non-superelastic materials. Although metallic ribbons are preferred as the ancillary materials because of their strength-to-weight ratios, fibrous materials (both synthetic and natural) may also be used. Preferred, because of cost, strength, and ready availability are stainless steels (SS304, SS306, SS316, etc.) and tungsten alloys. In certain applications, particularly smaller diameter catheter sections, more malleable metals and alloys, e.g., gold, platinum, palladium, rhodium, etc. may be used. A platinum alloy with a few percent of tungsten is preferred partially because of its radiopacity.

Suitable non-metallic ribbons include high performance materials such as those made of polyaramids (e.g., KEVLAR) and carbon fibers.

The braids utilized in this invention may be made using commercially available tubular braiders. Whenever the term "braid" is used herein, we mean tubular constructions in which the ribbons making up the construction are woven in an in-and-out fashion as they cross to form a tubular member defining a single lumen. The braids may be made up of a suitable number of ribbons, typically six or more. Ease of production on a commercial braider typically results in braids having eight or sixteen ribbons.

The braid shown in FIG. 2 has a nominal pitch angle of 45°. Clearly the invention is not so limited. Other braid angles from 20° to 60° are also suitable. An important variation of this invention is the ability to vary the pitch angle of the braid either at the time the braid is woven or at the time the braid is included in the guidewire section or sections.

The braid (132) may be rough to the touch if not covered or further processed. Procedures such as rolling, sanding, or grinding may be used to smooth the surface of the braid if so desired. Removal of any produced particulates is, of course, necessary. Whether the outer surface of the braid (132) is smoothed or not, it is quite desirable to place an outer layer of a lubricious polymer on the exterior of the braiding. The variation show in FIG. 2 utilizes the tie layer (134) discussed elsewhere herein and has a thin layer of a hydrophilic polymeric layer placed on the exterior of the tie layer (134). The hydrophilic polymeric layer is not depicted on the drawing because the layer is typically too thin to see. The tie layer (134) and its associated hydrophilic polymeric layer may be (but need not be) of the same composition through out the resulting guidewire assembly.

Guidewire Core Coatings

All or part of the guidewire core and braid may be covered or coated with one or more layers of a polymeric material. The coating is applied typically to enhance the lubricity of the guidewire assembly during its traversal of the catheter lumen or the vascular walls.

Coating Materials

As noted above, at least a portion of the guidewire core and braid may simply be coated by dipping or spraying or by similar process with such materials as polysulfones, polyfluorocarbons (such as TEFLON), polyolefins such as polyethylene, polypropylene, polyesters (including polyamides such as the NYLON's), and polyurethanes; their blends and copolymers such as polyether block amides (e.g., PEBAX).

It is often desirable to utilize a coating such as discussed just above on the proximal portion of the guidewire and a coating such as discussed below on the more distal sections. Any mixture of coatings placed variously on the guidewire is acceptable as chosen for the task at hand.

The guidewire core and braid may also be at least partially covered with other hydrophilic polymers including those made from monomers such as ethylene oxide and its higher homologs; 2-vinyl pyridine; N-vinylpyrrolidone; polyethylene glycol acrylates such as mono-alkoxy polyethylene glycol mono(meth)acrylates, including mono-methoxy triethylene glycol mono(meth)acrylate, mono-methoxy tetraethylene glycol mono(meth)acrylate, polyethylene glycol mono(meth)acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes. These monomers may be formed into homopolymers or block or random copolymers. The use of oligomers of these monomers in coating the guidewire for further polymerization is also an alternative. Preferred precursors include ethylene oxide; 2-vinyl pyridine; N-vinylpyrrolidone and acrylic acid and its salts; acrylamide and acrylonitrile polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred are ethylene, propylene, styrene, and styrene derivatives.

The polymeric coating may be cross-linked using various techniques, e.g., by light such as ultraviolet light, heat, or ionizing radiation, or by peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the monomers and polymers discussed above.

Polymers or oligomers applied using the procedure described below are activated or functionalized with photoactive or radiation-active groups to permit reaction of the polymers or oligomers with the underlying polymeric surface. Suitable activation groups include benzophenone, thioxanthone, and the like; acetophenone and its derivatives specified as:

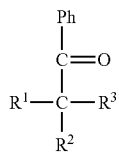

where
$R^1$ is H, $R^2$ is OH, $R^3$ is Ph; or
$R^1$ is H, $R^2$ is an alkoxy group including —$OCH_3$, —$OC_2H_3$, $R^3$ is Ph; or
$R^1=R^2=$an alkoxy group, $R^3$ is Ph; or
$R^1=R^2=$an alkoxy group, $R^3$ is H; or
$R^1=R^2=$Cl, $R^3$ is H or Cl.

Other known activators are suitable.

The polymeric coating may then be linked with the substrate using known and appropriate techniques selected on the basis of the chosen activators, e.g., by ultraviolet light, heat, or ionizing radiation. Crosslinking with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The polymeric coating may be applied to the guidewire by any of a variety of methods, e.g., by spraying a solution or suspension of the polymers or of oligomers of the monomers onto the guidewire core or by dipping it into the solution or suspension. Initiators may be included in the solution or applied in a separate step. The guidewire may be sequentially or simultaneously dried to remove solvent after application of the polymer or oligomer to the guidewire and crosslinked.

The solution or suspension should be very dilute since only a very thin layer of polymer is to be applied. We have found that an amount of oligomer or polymer in a solvent of between 0.25% and 5.0% (wt), preferred is 0.5 to 2.0% (wt), is excellent for thin and complete coverage of the resulting polymer. Preferred solvents for this procedure when using the preferred polymers and procedure are water, low molecular weight alcohols, and ethers, especially methanol, propanol, isopropanol, ethanol, and their mixtures. Other water miscible solvents, e.g., tetrahydrofuran, methylene dichloride, methylethylketone, dimethylacetate, ethyl acetate, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups and the like must be recognized by the user of this process when choosing polymers and solvent systems.

Particularly preferred as a coating for the guidewire cores discussed herein are physical mixtures of homo-oligomers of at least one of polyethylene oxide; poly 2-vinyl pyridine; polyvinylpyrrolidone, polyacrylic acid, polyacrylamide, and polyacrylonitrile. The catheter bodies or substrates are preferably sprayed or dipped, dried, and irradiated to produce a polymerized and crosslinked polymeric skin of the noted oligomers.

The lubricious hydrophilic coating is preferably produced using generally simultaneous solvent removal and crosslinking operations. The coating is applied at a rate allowing "sheeting" of the solution, e.g., formation of a visibly smooth layer without "runs". In a dipping operation for use with most polymeric substrates including those noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 250 C and the glass transition temperature ($T_g$) of the underlying substrate. Preferred temperatures are 500 C to 1250 C. Most preferred for the noted and preferred solvent systems is the range of 750 to 1100 C.

Ultraviolet light sources may be used to crosslink the polymer precursors onto the substrate. Movement through an irradiation chamber having an ultraviolet light source at 90-375 nm (preferably 300-350 nm) having an irradiation density of 50-300 mW/cm$^2$ (preferably 150-250 mW/cm$^2$) for a period of three to seven seconds is desired. Passage of a guidewire core through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

Exceptional durability of the resulting coating is produced by repetition of the dipping/solvent removal/irradiation steps up to five times. Preferred are two to four repetitions.

Tie Layers

We have found that it is often desirable to incorporate a "tie" layer as a coating between the outer polymeric surface and the braid to enhance the overall adhesion of the outer polymeric surface to the guidewire assembly. Of course, these materials must be able to tolerate the various other solvents, cleaners, sterilization procedures, etc. to which the guidewire and its components are placed during other production steps.

FIG. 2 shows a typical guide wire core section (100) made according to the invention having a metallic core (130), a braid (132), a polymeric tie layer (134), upon which a lubricious coating is placed.

Choice of materials for such tie layers is determined through their functionality. Specifically, the materials are chosen for their affinity or tenacity to the outer polymeric lubricious or hydrophilic coating. Clearly, the tie layer material must be flexible and strong. The tie layers may be placed onto the guidewire center in a variety of ways. The polymeric material may be extrudable and made into shrinkable tubing for mounting onto the guidewire through heating. It may be placed onto the guidewire core by dipping, spraying, shrink wrapping of polymeric tubing or other procedure. One quite desirable procedure involves the placement of a polymeric tubing of a fusible polymer, e.g., polyurethane, on the guidewire core which, in turn, is covered with a heat shrink tubing such as polyethylene. The outer tubing is shrunk down and the inner tubing is fused onto the guidewire core to form a tie layer. The tie layer is preferably 0.0004" to 0.003" in thickness. The melt temperature of the tie layer polymer desirably is appropriately chosen to fuse at the heat shrink temperature of the outer tubing. The outer shrink tubing is then simply peeled off, leaving the tie layer exposed for treatment with the lubricious coating.

We have found that various NYLON's, polyethylene, polystyrene, polyurethane, and polyethylene terephthalate (PET) make excellent tie layers. Preferred are polyurethane (Shore 80A-55D) and PET. Most preferred is polyurethane. It is additionally desirable to use a number of sections of polyurethane having differing hardnesses. For instance, the distal section may have a tie layer of Shore 80A polyurethane; the proximal shaft might be Shore D55 polyurethane. These materials may be formulated or blended to include radio opaque materials such as barium sulfate, bismuth trioxide, bismuth carbonate, tungsten, tantalum or the like.

As noted above, another manner of applying a tie layer is by heat-shrinking the tubing onto the braid. The guidewire core and the exterior braid is simply inserted into a tubing of suitable size—often with a small amount of a "caulking" at either end to seal the tubing. The tubing is cut to length and heated until it is sufficiently small in size. The resulting tubing tie layer desirably is between about 0.0005 and 0.015 inches in thickness. The thinner layers are typically produced from polyurethane or PET. The layer of lubricious polymer is then placed on the outer surface of the shrunk tubing.

Another procedure for preparing or pretreating guidewires prior to receiving a subsequent coating of a polymer, preferably a polymer which is lubricious, biocompatible, and hydrophilic, is via the use of a plasma stream to deposit a hydrocarbon or fluorocarbon residue. The procedure is described as follows: the guidewire core and braid is placed in a plasma chamber and cleaned with an oxygen plasma etch. It is then exposed to a hydrocarbon plasma to deposit a plasma-polymerized tie layer on the guidewire core to complete the pretreatment. The hydrocarbon plasma may comprise a lower molecular weight (or gaseous) alkanes such as methane, ethane, propane, isobutane, butane or the like; lower molecular weight alkenes such as ethene, propene, isobutene, butene or the like or; gaseous fluorocarbons such as tetrafluoromethane, trichlorofluoromethane, dichlorodifluoromethane, trifluorochloromethane, tetrafluoroethylene, trichlorofluoroethylene, dichlorodifluoroethylene, trifluorochloroethylene and other such materials. Mixtures of these materials are also acceptable. The tie layer apparently provides C—C bonds for subsequent covalent bonding to the outer hydrophilic polymer coating. Preferred flow rates for the hydrocarbon into the plasma chamber are in the range of 500 c.c./min. to 2000 c.c./min. and the residence time of the guidewire in the chamber is in the range of 1-20 minutes, depending on the chosen hydrocarbon and the plasma chamber operating parameters. Power settings for the plasma chamber are preferably in the range of 200 W to 1500 W.

A tie layer of plasma-produced hydrocarbon residue having a thickness on the order of $10\mu$ thick is disposed between braid and coating. This process typically produces layers of hydrocarbon residue less than about $1000\mu$ in thickness, and more typically less than about $100\mu$. The tie layer effectively bonds the outer layer to the guidewire core while adding very little additional bulk to the guidewire. Guidewires made according to this invention therefore avoid the size and maneuverability problems of prior art guidewires.

The pretreated guidewire may be coated with a polymer using a procedure such as described above. For example, the pretreated guidewire may be dipped in a solution of a photoactive hydrophilic polymer system, i.e., a latently photoreactive binder group covalently bonded to a hydrophilic polymer. After drying, the coated guidewire is cured by exposing it to UV light. The UV light activates the latently reactive group in the photoactive polymer system to form covalent bonds with crosslinked C—C bonds in the hydrocarbon residue tie layer. The dipping and curing steps are preferably repeated often enough, typically twice, to achieve the appropriate thickness of the hydrophilic coating layer.

One highly preferred variation of the invention involves a guidewire with metal core, preferably 0.010" to 0.025" diameter stainless steel or high elasticity alloy (such as nitinol) and a braid of stainless steel or a high elasticity alloy. The exterior surface of the guidewire is a biocompatible coating of a polyacrylamide/polyvinyl-pyrrolidone mixture bonded to a photoactive binding agent.

A preferred photoactive hydrophilic polymer system is a mixture of a polyacrylamide and polyvinylpyrrolidone. The polyacrylamide system provides lubricity, and the polyvinylpyrrolidone system provides both lubricity and binding for durability. As an alternative, however, the hydrophilic biocompatible coating may be polyacrylamide alone, polyvinylpyrrolidone alone, polyethylene oxide, or any suitable coating known in the art. In addition, a coating of heparin, albumin or other proteins may deposited over the hydrophilic coating in a manner known in the art to provide additional biocompatibility features.

The guidewire may be cleaned by using an argon plasma etch in place of the oxygen plasma etch. The thickness of the plasma-polymerized tie layer may also vary without departing from the scope of this invention.

Although preferred embodiments of the present invention have been described, it should be understood that various changes, adaptations, and modifications may be made therein without departing from the spirit of the invention and the scope of the claims which follow.

We claim:

1. A guidewire suitable for guiding a catheter within a body lumen, comprising:
    an elongated, flexible core wire having a proximal section including a stainless steel alloy, a distal section including a stainless steel alloy, and a section intermediate the proximal section and the distal section including a super-elastic alloy;
    a tubular braid having a length and a wall thickness, the length of the tubular braid extending from a location proximal of the distal section of the core wire to a distal end of the distal section of the core wire, the tubular braid coaxially disposed about the core wire such that the maximum radial gap between the tubular braid and the core wire is less than the wall thickness of the tubular braid along the entire length of the tubular braid; and
    a distal coil disposed coaxially over the core wire.

2. The guidewire of claim 1, wherein the braid includes a super-elastic alloy.

3. The guidewire of claim 2, further comprising a polymeric layer situated exterior to at least a portion of the braid.

4. The guidewire of claim 3, wherein the polymeric layer comprises a hydrophilic polymer.

5. The guidewire of claim 1, wherein the braid is in contact with the core wire along its length.

6. The guidewire of claim 5, wherein the braid is formed by directly winding the braid onto the core wire.

7. The guidewire of claim 1, further comprising a layer of polymer between the braid and the core wire that bonds the braid to the core wire.

8. The guidewire of claim 1, wherein the braid is glued to the core wire.

9. The guidewire of claim 1, wherein the braid is welded to the core wire.

10. The guidewire of claim 1, wherein the braid is bonded to the core wire and wherein the bonding is continuous.

11. The guidewire of claim 1, wherein the braid is bonded to the core wire and wherein the bonding is at intervals.

12. The guidewire of claim 1, wherein the guidewire includes a tapered portion and wherein the tubular braid tapers to follow the guidewire tapered portion.

13. The guidewire of claim 1, wherein the distance between the guidewire and the tubular braid is uniform along the length of the tubular braid.

\* \* \* \* \*